(12) United States Patent
Stut et al.

(10) Patent No.: US 10,930,131 B2
(45) Date of Patent: Feb. 23, 2021

(54) METHOD AND APPARATUS FOR PROVIDING FEEDBACK TO A USER ABOUT A FALL RISK

(71) Applicant: KONINKLIJKE PHILIPS N.V., Eindhoven (NL)

(72) Inventors: Wilhelmus Johannes Joseph Stut, Eindhoven (NL); Janneke Annegarn, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/625,042

(22) PCT Filed: Jun. 22, 2018

(86) PCT No.: PCT/EP2018/066691
§ 371 (c)(1),
(2) Date: Dec. 20, 2019

(87) PCT Pub. No.: WO2019/002108
PCT Pub. Date: Jan. 3, 2019

(65) Prior Publication Data
US 2020/0219373 A1 Jul. 9, 2020

(30) Foreign Application Priority Data
Jun. 28, 2017 (EP) .................................... 17178530

(51) Int. Cl.
*G08B 23/00* (2006.01)
*G08B 21/04* (2006.01)
(Continued)

(52) U.S. Cl.
CPC ........ *G08B 21/0423* (2013.01); *A61B 5/1117* (2013.01); *A61B 5/486* (2013.01);
(Continued)

(58) Field of Classification Search
CPC .................................................. G08B 21/0423
(Continued)

(56) References Cited

U.S. PATENT DOCUMENTS

| 8,409,116 B2 | 4/2013 | Wang et al. |
| 2010/0049096 A1 | 2/2010 | Ten Kate |

(Continued)

FOREIGN PATENT DOCUMENTS

| EP | 2687157 A2 | 1/2014 |
| JP | 2014188158 A | 10/2014 |
| WO | 2013011398 A1 | 1/2013 |

OTHER PUBLICATIONS

International Search Report and Written Opinion, International Application No. PCT/EP2018/066691, dated Aug. 21, 2018.

(Continued)

*Primary Examiner* — Tai T Nguyen

(57) ABSTRACT

The invention relates to a method and apparatus for providing feedback to a user, in particular relating to the fall risk of the user and/or relating to advice to reduce the fall risk of the user. According to an embodiment, there is provided an apparatus for providing feedback to a user, the apparatus comprising a user interface for providing feedback to the user; and a processing unit. The processing unit is configured to obtain measurements of the fall risk of the user over a time period, the time period comprising at least one time portion in which the fall risk of the user increases to a first threshold value while moving, the user rests for a resting period when the fall risk reaches the first threshold value, and the user subsequently resumes moving; analyse the measurements of the fall risk of the user to determine the duration of each resting period and the fall risk of the user at the end of each resting period when the user subsequently resumes moving; determine a fall risk recovery profile for the user from the duration of each resting period and the fall (Continued)

risk of the user at the end of each resting period; determine the duration of a resting period required for the fall risk of the user to decrease to a second threshold value using the fall risk recovery profile; and provide feedback to the user on the determined duration via the user interface.

15 Claims, 6 Drawing Sheets

(51) Int. Cl.
| | |
|---|---|
| *G16H 20/30* | (2018.01) |
| *G16H 50/30* | (2018.01) |
| *G16H 40/63* | (2018.01) |
| *A61B 5/11* | (2006.01) |
| *A61B 5/00* | (2006.01) |

(52) U.S. Cl.
CPC .......... *A61B 5/7267* (2013.01); *A61B 5/7275* (2013.01); *A61B 5/742* (2013.01); *A61B 5/7405* (2013.01); *A61B 5/7455* (2013.01); *G08B 21/0446* (2013.01); *G16H 20/30* (2018.01); *G16H 40/63* (2018.01); *G16H 50/30* (2018.01); *A61B 2503/08* (2013.01)

(58) Field of Classification Search
USPC .......... 340/573.1, 573.4, 517, 521, 435–438, 340/540, 541; 600/595, 598
See application file for complete search history.

(56) References Cited

U.S. PATENT DOCUMENTS

| | | |
|---|---|---|
| 2012/0133514 A1 | 5/2012 | Palshof |
| 2013/0023798 A1* | 1/2013 | Greene ................. A61B 5/1117 600/595 |
| 2015/0199892 A1 | 7/2015 | Johnson et al. |
| 2016/0100776 A1 | 4/2016 | Najafi et al. |
| 2016/0220153 A1 | 8/2016 | Annegarn et al. |
| 2017/0061763 A1 | 3/2017 | Hanson et al. |
| 2018/0177436 A1* | 6/2018 | Chang ................... A61B 5/112 |

OTHER PUBLICATIONS

Brodie, M. et al., "Disentangling the health benefits of walking from increased exposure to falls in older people using remote gait monitoring and multi-dimensional analysis", Physiological Measurement, 2017.

Hamacher, D. et al., "The effect of physical exhaustion on gait stability in young and older individuals", Gait and Posture, 2016, 137-139.

* cited by examiner

METHOD AND APPARATUS FOR PROVIDING FEEDBACK TO A USER ABOUT A FALL RISK

CROSS-REFERENCE TO PRIOR APPLICATIONS

This application is the U.S. National Phase application under 35 U.S.C. § 371 of International Application No. PCT/EP2018/066691, filed on 22 Jun. 2018, which claims the benefit of European Patent Application No. 17178530.6, filed on 28 Jun. 2017. These applications are hereby incorporated by reference herein.

TECHNICAL FIELD OF THE INVENTION

The invention relates to a method and apparatus for providing feedback to a user, in particular relating to the fall risk of the user and/or relating to advice to reduce the fall risk of the user.

BACKGROUND TO THE INVENTION

Falls are a significant problem, particularly for elderly people. About 30 percent of people over 65 years old fall at least once a year. Home-based fall-prevention exercise programs that include balance training, muscle strengthening and a walking plan have been found to be effective in reducing the occurrence of falls by 30-46%. Fall risk assessment (i.e. assessing the risk of a user falling at any given time) is important to identify elderly people at risk of falling, to tailor exercises for optimizing fall prevention intervention programs and to monitor progression of fall risk. The risk of a user falling at any given time can vary both in the long term (e.g. due to aging, injuries, etc.) but also in the short term (e.g. due to fatigue, lighting conditions around the person, weather conditions, the evenness of the ground, etc.).

Performing walking exercises (i.e. going for walks) is known to provide many health benefits, but can both increase fall rates (since a user may be at higher risk of falling while walking) and decrease fall rates (since the user will be more physically capable). It is also known that the risk of falling increases when a person is tired.

SUMMARY OF THE INVENTION

Although systems are currently available that can provide a user with an indication of their fall risk at a particular time, for example as disclosed in WO 2014/195146, the feedback provided to the user by such systems can be improved. In particular, it may be useful to provide an indication to the user of their fall risk due to e.g. physical fatigue, and whether the user should take a rest. It may also or alternatively be useful to provide an indication to the user how long they should rest for to reduce their fall risk to an acceptable level before resuming walking. It may also or alternatively be useful to provide an indication or information to the user about how to reduce their fall risk in future walking exercises.

Thus, according to a first aspect, there is provided an apparatus for providing feedback to a user, the apparatus comprising a user interface for providing feedback to the user; and a processing unit configured to obtain measurements of the fall risk of the user over a time period and information on the duration of resting periods occurring during the time period, the time period comprising at least one time portion in which the fall risk of the user increases to a first threshold value while moving, the user rests for a resting period when the fall risk reaches the first threshold value, and the user subsequently resumes moving; analyse the measurements of the fall risk of the user to determine the fall risk of the user at the end of each resting period when the user subsequently resumes moving and the duration of the resting period; determine a fall risk recovery profile for the user from the duration of each resting period and the fall risk of the user at the end of each resting period; determine the duration of a resting period required for the fall risk of the user to decrease to a second threshold value using the fall risk recovery profile; and provide feedback to the user on the determined duration via the user interface.

According to a second aspect, there is provided a method of providing feedback to a user, the method in an apparatus comprising obtaining measurements of the fall risk of the user over a time period and information on the duration of resting periods occurring during the time period, the time period comprising at least one time portion in which the fall risk of the user increases to a first threshold value while moving, the user rests for a resting period when the fall risk reaches the first threshold value, and the user subsequently resumes moving; analysing the measurements of the fall risk of the user to determine the fall risk of the user at the end of each resting period when the user subsequently resumes moving and the duration of the resting period; determining a fall risk recovery profile for the user from the duration of each resting period and the fall risk of the user at the end of each resting period; determining the duration of a resting period required for the fall risk of the user to decrease to a second threshold value using the fall risk recovery profile; and providing feedback to the user on the determined duration via a user interface in the apparatus.

According to a third aspect, there is provided a computer program product comprising a computer readable medium having computer readable code embodied therein, the computer readable code being configured such that, on execution by a suitable computer or processing unit, the computer or processing unit is caused to perform the method described above.

According to a fourth aspect, there is provided an apparatus for providing feedback to a user, the apparatus comprising a user interface for providing feedback to the user; and a processing unit configured to obtain measurements of the fall risk of the user over a time period, the time period comprising at least one time portion in which the fall risk of the user increases to a first threshold value while moving; analyse the measurements of the fall risk of the user to determine a fall risk increase profile for the user; determine the maximum duration of a moving period for the user to reduce the likelihood of the fall risk exceeding the first threshold value while the user is moving; and provide feedback to the user on the determined maximum duration via the user interface.

According to a fifth aspect, there is provided a method of providing feedback to a user, the method in an apparatus comprising obtaining measurements of the fall risk of the user over a time period, the time period comprising at least one time portion in which the fall risk of the user increases to a first threshold value while moving; analysing the measurements of the fall risk of the user to determine a fall risk increase profile for the user; determining the maximum duration of a moving period for the user to reduce the likelihood of the fall risk exceeding the first threshold value while the user is moving;

and providing feedback to the user on the determined maximum duration via a user interface in the apparatus.

These and other aspects of the invention will be apparent from and elucidated with reference to the embodiment(s) described hereinafter.

BRIEF DESCRIPTION OF THE DRAWINGS

Exemplary embodiments of the invention will now be described, by way of example only, with reference to the following drawings, in which.

DETAILED DESCRIPTION OF EMBODIMENTS

Figure 1:
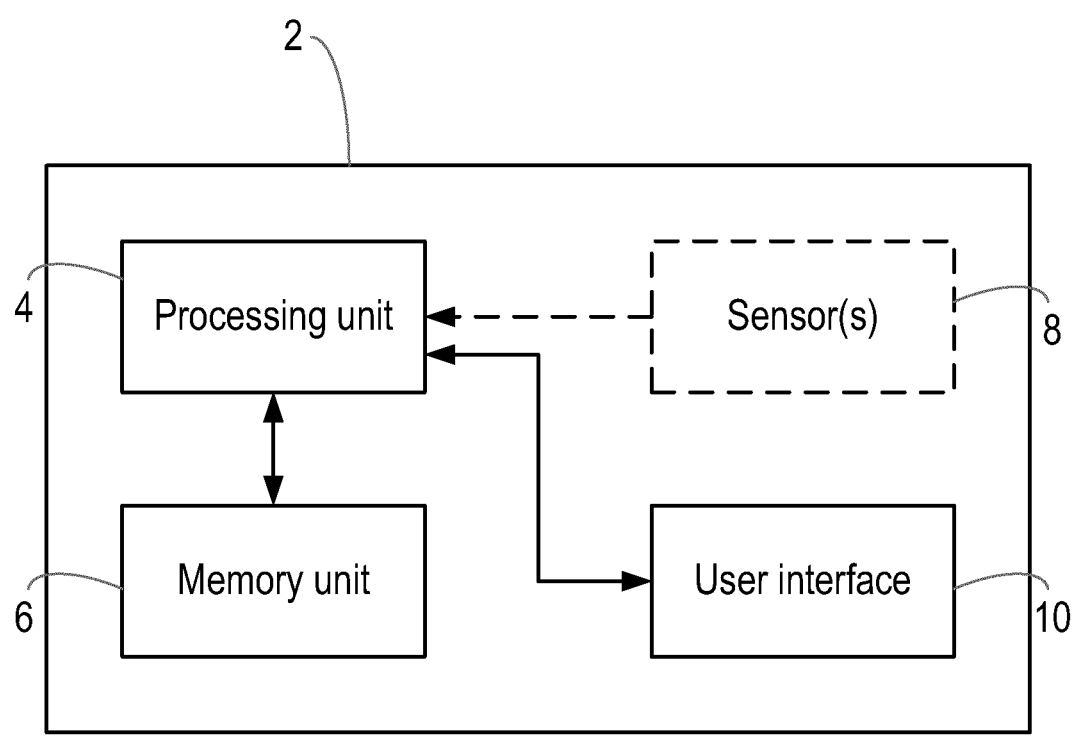
FIG. 1 is a block diagram of an apparatus according to an embodiment.

FIG. 1 shows an apparatus 2 for providing feedback to a user according to an embodiment. The apparatus 2 comprises a processing unit 4 and a memory unit 6 that are connected to each other. The processing unit 4 controls the operation of the apparatus 2 and generally implements the method according to the invention. The processing unit 4 can be implemented in numerous ways, with software and/or hardware, to perform the various functions described below. The processing unit 4 may comprise one or more microprocessors or digital signal processor (DSPs) that may be programmed using software or computer program code to perform the required functions and/or to control components of the processing unit 4 to effect the required functions. The processing unit 4 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

In various implementations, the processing unit 4 may be associated with or comprise one or more memory units 6 such as volatile and non-volatile computer memory such as RAM, PROM, EPROM, and EEPROM. The processing unit 4 or associated memory unit 6 can also be used for storing program code that can be executed by a processor in the processing unit 4 to perform the methods described herein. In some embodiments, the memory unit 6 can store information generated during execution of the methods, information for use during execution of the methods (e.g. one or more threshold values, one or more types of feedback messages and/or content for feedback messages), and/or data received from one or more sensors or external information sources.

As described in more detail below, the apparatus 2 provides feedback to a user derived from their fall risk. As such, the apparatus 2 requires measurements of the fall risk of the user over a time period. In some embodiments, the apparatus 2 can receive these measurements from another apparatus or device that monitors the user and determines the fall risk. In that case, the processing unit 4 can be configured to receive measurements of the fall risk from the other apparatus or device, for example via an input to the apparatus 2, or via wireless transmission from the other apparatus or device to the apparatus 2. Alternatively, the apparatus 2 can be configured to determine the fall risk of the user. In that case, the apparatus 2 can comprises one or more sensors 8 for measuring the movements of the user, and/or for measuring one or more environmental parameters that can affect the fall risk of the user, and the processing unit 4 is configured to determine the fall risk from those measurements. The one or more sensors 8 can include a movement sensor, such as an accelerometer and/or gyroscope, for directly measuring the movements of the user, a position or location sensor, such as a satellite positioning system receiver (e.g. GPS, Galileo, etc.), an air pressure sensor for measuring air pressure (that can be used to identify changes in altitude of the user, for example walking up or down stairs), etc. The one or more sensors 8 can also or alternatively comprise a sensor or sensors that can measure the weather conditions, the lighting conditions around the user, whether the user is using a walking aid, etc. Techniques and algorithms for determining the fall risk of a user from measurements of movements and/or the status of the user and/or environmental parameters are known in the art, e.g. in WO 2014/195146 and WO 2010/026513, and are not described in detail herein.

The apparatus 2 also comprises a user interface 10 for providing the feedback determined by the processing unit 4 to the user. The user interface 10 can therefore be or comprise a display screen or one or more other elements (e.g. lights or LEDs) for providing visual feedback, a speaker for providing audio feedback, a vibrating element for providing tactile feedback, or any combination thereof. The user interface 10 may also enable the user to interact with the apparatus 2, for example to activate or deactivate the apparatus 2, to control one or more settings or operations of the apparatus 2 and/or to enable the user to input information that is useful for customising or tailoring the feedback to the user and/or useful for assessing fall risk (if the apparatus 2 determines the fall risk). As such the user interface 10 can comprise any one or more of a touch screen, button(s), switch(es), keypad, keyboard, mouse, trackpad, stylus, etc.

It will be appreciated that in some embodiments all of the components of the apparatus 2 (e.g. the processing unit 4, memory unit 6, sensor(s) 8 (if present) and user interface 10) can be contained within a single housing or device. For example the apparatus 2 could be in the form of a smartphone, tablet computer, pendant, bracelet, smart watch, etc. that can be carried or worn by the user. In alternative embodiments, the components of the apparatus 2 may be distributed between two or more housings or devices. For example, the processing unit 4 and memory unit 6 could be part of a first device (e.g. a computer, remote server, laptop, tablet computer, smartphone, etc.), and the user interface 10 could be part of a second device (e.g. a wearable device that is carried by the user, such as a pendant, bracelet, or smart watch).

It will be appreciated that the apparatus 2 may comprise additional components to those shown in FIG. 1. For example the apparatus 2 may comprise a power source, such as a battery, or a power interface component, such as plug, for connecting the apparatus 2 to a mains power supply. If the apparatus 2 is required to exchange data or information with another device, e.g. a device that determines the fall risk, or sensors, devices and/or information sources that provide information relevant for determining fall risk, the apparatus 2 can comprise components or circuitry for enabling the information exchange via a wired or wireless connection (for example via WiFi, Bluetooth, a cellular communication protocol, etc.).

Figure 2:
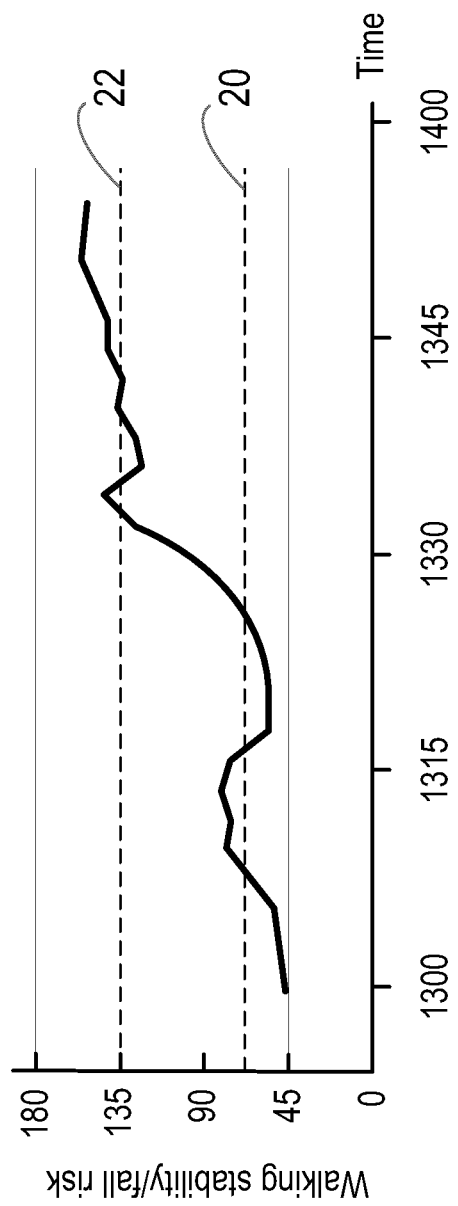
FIG. 2 is a graph illustrating walking stability/fall risk over time.

FIG. 2 is a graph illustrating walking stability/fall risk over a period of time of approximately one hour in which the user was walking. The measurements of fall risk used to derive this graph can be determined as described above. It can be seen that the fall risk of the user varies, and in this example the fall risk generally increases over the one hour time period. Where the walking stability/fall risk is below the lower dashed line 20, the fall risk is considered to be low, above the lower dashed line 20 and below upper dashed line 22 is considered to be an intermediate fall risk, and above the upper dashed line 22 the user is considered to be at a high (or potentially imminent) risk of falling. It will be appreciated that the positions of the lines 20, 22 in FIG. 2 is merely exemplary, and can depend on system settings and/or preferences and/or capabilities of the user.

In some embodiments, the apparatus 2 can be used to provide feedback to the user about their fall risk during a walking session or activity. This feedback can be provided in real-time, i.e. as the fall risk is determined by the apparatus 2 (or received from another device or apparatus). As an example, the feedback can be provided in the form of an audible tone or message. In some cases the feedback may only be provided once the fall risk is deemed to be high (e.g. above a threshold). As another example, the feedback can be provided in a visual form, for example the user could be presented with the graph shown in FIG. 2, illustrating to the user how their fall risk has changed over the last few minutes or hour. Feedback could also or alternatively be provided in the form of a map that can illustrate the user's fall risk during their walk (e.g. showing locations where the fall risk was high, etc.).

As a specific example, it is possible for the fall risk to be measured shortly (e.g. a few seconds) after a user starts walking. If this fall risk is X % higher than a normal fall risk for the user (e.g. a long-term average value of the fall risk), then the apparatus 2 could alert the user to this. In some cases, the apparatus 2 can use the user interface 10 to request information from the user on the reasons for this heightened fall risk. Based on the responses from the user, the apparatus 2 could give feedback indicating that the user should return to their home and change shoes, first do some stretching exercises, walk on a regular surface, postpone the walk or consider an alternative mode of transport (e.g. car, bus, taxi).

As another example, if the apparatus 2 determines that there has been a sudden or abrupt increase in the fall risk, typically not due to fatigue, but due to abrupt changes in the environment or due to the user falling, the apparatus 2 can provide appropriate feedback to the user. Additionally, the apparatus 2 can use the user interface 10 to request information from the user on the reasons for this heightened fall risk. The apparatus 2 can use the responses from the user to adapt the feedback accordingly. Based on the responses from the user and the environment, the apparatus 2 could give appropriate feedback. For example if the surface has changed, the user can be advised to walk on a regular surface. If the weather has changed (e.g. has become stormy), the user can be advised to walk a bit slower, walk arm-in-arm with a friend, or consider an alternative mode of transportation (e.g. car, bus, taxi). If the user has fallen and has resumed walking, but, for example due to injury, the user is now at a higher risk of falling, the user can be advised to walk arm-in-arm with a buddy or consider an alternative way of transportation (car, bus, taxi).

One useful type of feedback that can be provided to a user during walking is the length of time that they should rest during a walk in order to reduce their risk of falling. This type of feedback is useful where a user's fall risk tends to increase during a walk, typically due to fatigue. FIG. 2 is an example of such a fall risk profile. If the fall risk reaches a threshold value (e.g. dashed line 22), then the apparatus 2 can determine this and provide feedback to the user that they should rest (e.g. sit down for a few minutes). The user should ideally only resume walking once their fall risk has decreased significantly (i.e. their levels of fatigue have reduced). However, fall risk can only be determined when the user is moving (walking) so it is not possible to determine how long the rest period should be using conventional techniques.

Figure 3:
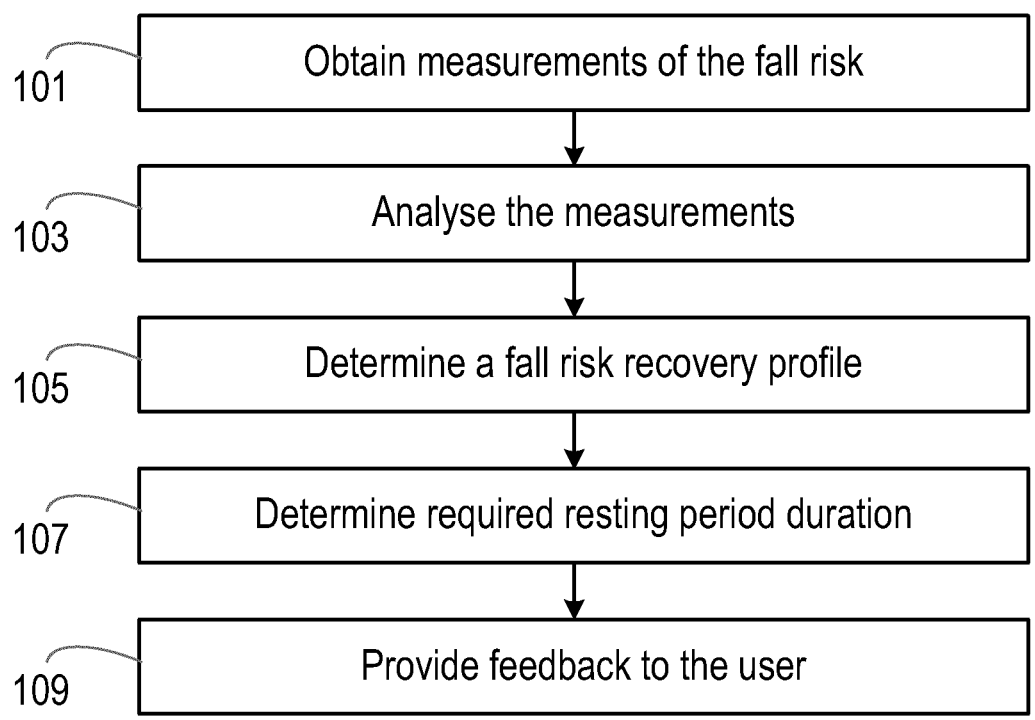
FIG. 3 is a flow chart illustrating a method of providing feedback to a user according to a first aspect.

The flow chart in FIG. 3 illustrates a method according to a first aspect of the invention for addressing this problem. It will be appreciated that the method in FIG. 3 can be performed by apparatus 2, in particular by processing unit 4. The memory unit 4 or other data storage device can be used to store computer-readable code that, when executed by the processing unit 4 or other computing device, causes the processing unit 4 or other computing device to perform the method in FIG. 3.

In a first step, step 101, measurements of the fall risk of the user over a time period are obtained, along with information on the duration of resting periods that occurred during the time period. The time period should comprise at least one time portion in which the fall risk of the user increases to a first threshold value while moving, the user resting for a resting period when the fall risk reaches the first threshold value and the user subsequently resuming moving. Since these fall risk measurements are to be used to determine a fall risk recovery profile for the user, ideally the time period covers several such time portions. It will be appreciated that the fall risk measurements do not have to cover a continuous time period, but could, for example, relate to measurements of the fall risk of the user when the user is moving over several different hours and/or days.

The fall risk measurements may only relate only to times when the user is performing a moving activity (e.g. walking, jogging or running). For example they may not relate to times when the user is relaxing at home or sleeping (although these times may still be part of the time period. It will be appreciated that although these relaxing or sleeping times can be considered as 'resting', for the purposes of the invention the information on the duration of resting periods that occurred during the time period relate only to resting periods that occur following the fall risk of the user exceeding the first threshold value.

In some embodiments, the measurements of the fall risk and information on the duration of resting periods that occurred during the time period are obtained by retrieving them from the memory unit 6. In this embodiment, the measurements and information may have been received from another device or apparatus and stored in the memory unit 6 for subsequent processing, or determined by the apparatus 2 itself and stored in the memory unit 6 for subsequent processing. In alternative embodiments, the measurements of the fall risk and information on the duration of resting periods that occurred during the time period can be obtained by receiving them from another device or apparatus. In other alternative embodiments, the measurements and information are obtained by determining the measurements of the fall risk and duration of resting periods from measurements from one or more sensors 8 that measure the movements of the user and/or one or more environmental parameters. As noted above, techniques and algorithms for determining a measurement of a fall risk for a user are known in the art and are not described in detail herein. In addition, techniques and algorithms for determining whether a user is at rest are also known in the art and are not described in detail herein.

In some embodiments, the time period for which the measurements of the fall risk of the user are obtained in step 101 can be considered as a 'training phase' for the apparatus 2. During this training phase, the fall risk of the user can be measured and compared to the first threshold value, and if the fall risk exceeds the first threshold value, the apparatus 2 (or another apparatus or device if the fall risk is measured by another apparatus or device) can provide feedback to the user that they should rest (or otherwise stop their current movement (be it walking, jogging, running, etc.)). During this training phase the feedback does not indicate the duration of the rest, merely that a rest is advised. During this rest the fall risk of the user will typically decrease (since the increase in the fall risk is typically due to fatigue), and this can be measured once the user resumes moving after the rest. Of course, since measurements of fall risk are based on measurements of the movements of the user, it is not possible to measure the fall risk during the rest period.

After the measurements of fall risk have been obtained, the processing unit 4 analyses the measurements of the fall risk of the user to determine the fall risk of the user at the end of each resting period when the user subsequently resumes moving and the duration of each resting period (step 103). In this step the processing unit 4 effectively derives fall risk/resting period duration pairs, i.e. for each resting period the processing unit 4 determines the fall risk at the end of that period and the duration of the period.

Next, in step 105, the processing unit 4 determines a fall risk recovery profile for the user from the duration of each resting period and the fall risk of the user at the end of each resting period. The fall risk recovery profile represents how the fall risk of the user changes (i.e. decreases/recovers) over time. As the measurements and information obtained in step 101 relate to several resting periods of differing durations, it is possible to estimate how the fall risk of the user changes over time. Thus, step 105 can comprise fitting a curve to the fall risk/resting period duration pairs to determine the profile, or modelling a typical fall risk recovery using the fall risk/resting period duration pairs. Alternatively, step 105 can comprise sorting the data based on the duration of the resting period, and calculating the average fall risk (or confidence interval) from pairs with the same resting period duration.

Figure 4:
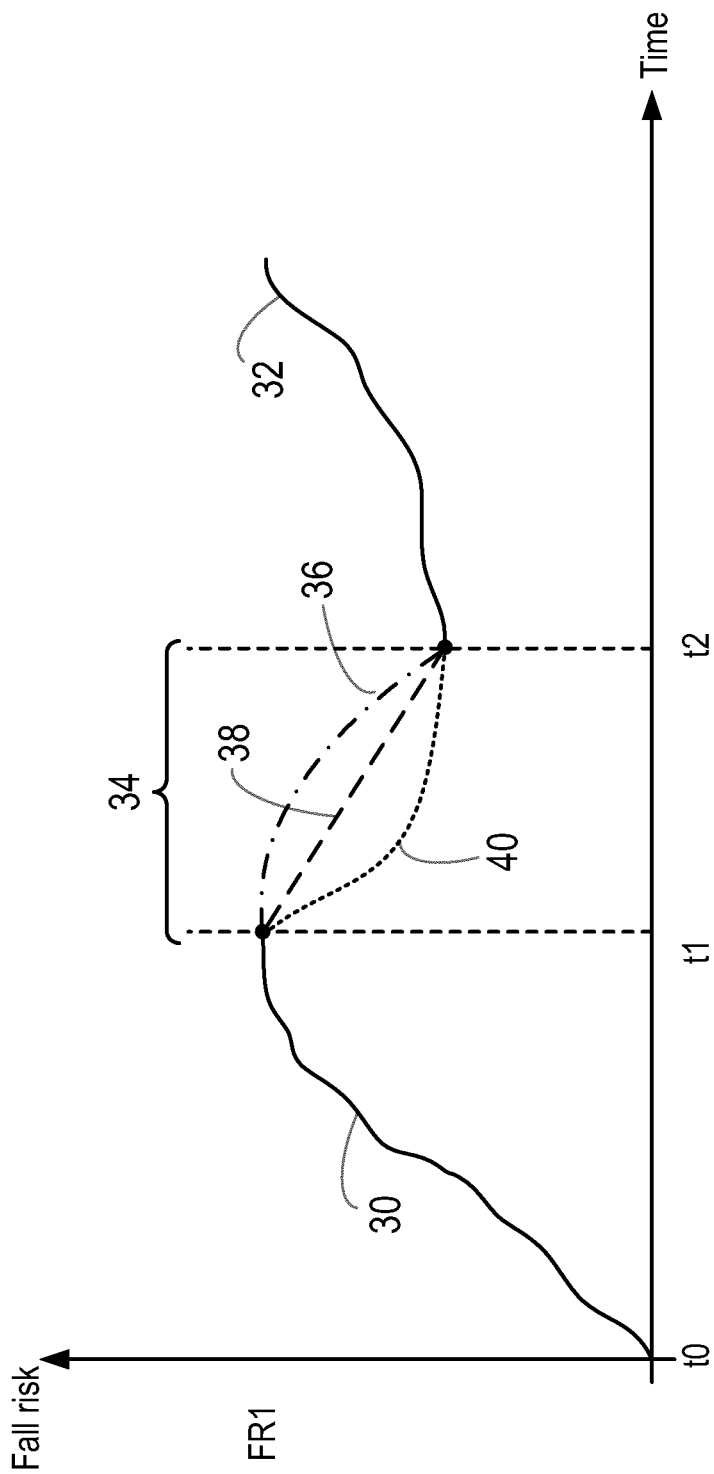
FIG. 4 is another graph illustrating fall risk over time.

The derivation of the fall risk recovery profile may also take into account the fall risk at the start of each resting period is stored since a user may not (or not be able to) rest as soon as their fall risk reaches the first threshold value and feedback is provided that they should rest. For example the user may be advised to rest, but they may need to continue walking for several minutes before they reach the next bench or seat (by which time their fall risk could have increased further). As an example, it could take 5 minutes to reduce the fall risk from 100 to 60 (a decrease of 40 units), but it could take 3 minutes to reduce the fall risk from 80 to 40 (also a decrease of 40 units). FIG. 4 is a graph illustrating the fall risk of a user over time while they are moving, resting and then moving again. The measurements of fall risk shown in FIG. 4 can correspond to a time portion set out above with reference to step 101. Thus, the measurements of fall risk increase from time $t_0$ to a first threshold value $FR_1$ at time $t_1$ due to fatigue, as shown by line 30. The user rests from time $t_1$, for example in response to feedback that their fall risk has exceeded threshold $FR_1$, and it is not possible to measure fall risk during the resting period. The user resumes moving at time $t_2$ where the fall risk has decreased to a value below the first threshold value, $FR_1$, and the fall risk gradually increases again, as shown by line 32. The resting period 34 thus corresponds to the period between $t_1$ and $t_2$ and has a duration of $t_2-t_1$. As noted above, the actual fall risk during the resting period is unknown, since the fall risk can only be measured when the user is moving, and the fall risk could follow any number of paths during the resting period, as shown by the three lines/curves 36, 38 and 40. As an example, the fall risk recovery profile (or part of the fall risk recovery profile) determined in step 105 from several resting periods of different durations may correspond to one of lines 36, 38 and 40.

Next, in step 107, the processing unit 4 uses the fall risk recovery profile to determine the duration of a resting period required for the fall risk of the user to decrease to a second threshold value. In some embodiments, the required resting period duration is determined in step 107 as the period required for the fall risk to decrease from the first threshold value to the second threshold value. The second threshold value is selected such that the user is able to rest and lower their fall risk to a value where they are at a lower risk of falling. However from a physical training perspective the duration of the resting period should not be too long and the user should resume moving as soon as possible. Thus the second threshold value can be selected to balance these two requirements. The amount by which the fall risk should be decreased (i.e. the size of the second threshold value relative to the first threshold value) can depend on the type of fall risk measurement being used, and/or on the user themselves. In some embodiments, step 107 comprises reading out the rest period duration associated with the fall risk equal to the second threshold value. In further embodiments, the duration can be adjusted based on environmental parameters (e.g. the duration could be increased if the weather is now stormy).

Once the duration has been predicted using the fall risk recovery profile, the processing unit 4 provides feedback to the user on the determined duration via the user interface 10 in the apparatus 2 (step 109). The feedback can be a visual, audible and/or tactile indication of the determined duration (e.g. a visual display of the duration, or a spoken message conveying the duration). Step 109 can be performed as soon as the duration is determined, or it can be performed when the user is advised to rest, for example when their fall risk is determined to exceed the first threshold value.

If the user does not rest straight away (i.e. immediately or within a threshold time period of the feedback being provided), after step 107 and 109 the method can further comprise obtaining further measurements of the fall risk of the user as the user continues to move and comparing the further measurements to the first threshold value. Step 107 can then be repeated to determine a new required resting period duration if their fall risk continues to increase and further feedback provided. For example the user may not be able to rest straight away (i.e. as soon as their fall risk exceeds the first threshold value and feedback is provided that they should rest) so the repetition of step 107 can comprise determining the required resting period duration starting from the last fall risk measurement obtained before the user starts to rest and this resting period duration can be communicated to the user. In particular, if the user continues walking or moving after their fall risk exceeds the first threshold value in order to reach a bench or seat, their fall risk may have further increased beyond the first threshold value, requiring a longer resting period in order for the fall risk to decrease to the second threshold value. In this case, when the fall risk first exceeds the first threshold value, feedback may be provided about a resting period duration required to reduce the fall risk from the first threshold value to the second threshold value, and this resting period duration can be revised if the fall risk of the user continues to increase. These further measurements of fall risk can be obtained in real time or near real time (i.e. so that the fall risk measurements reflect the user's current risk of falling). As with the measurements obtained in step 101, these further measurements can be obtained by retrieving the further measurements from the memory unit 6, by receiving the further measurements from another device or apparatus, or by determining the further measurements from measurements from one or more sensors 8 that measure the movements of the user and/or one or more environmental parameters.

In the example of FIG. 4, if the fall risk at time $t_2$ is considered to be at the second threshold value, then the profile determined in step 105 will indicate that the user should rest for a duration equal to $t_2-t_1$, and this feedback can be provided to the user in step 109.

In some embodiments, when further measurements of the fall risk are obtained (not just relating to measurements of the user continuing to move after feedback has been provided that they should rest, but measurements of the fall risk before and after a resting period), these measurements can be used to determine an updated fall risk recovery profile. The updated fall risk recovery profile can be determined by repeating step 105 using the measurements and information obtained in step 101 and the further measurements of the fall risk of the user.

Once an updated fall risk recovery profile has been determined, step 107 can be repeated using the updated profile to determine an updated resting period duration required for the fall risk of the user to decrease from the first threshold value to a second threshold value. This updated duration can then be fed back to the user using the user interface 10, either when the updated duration is determined, or when the fall risk of the user next exceeds the first threshold value.

In a further embodiment, the measurements of fall risk obtained in step 101 can be analysed with the aim to provide an indication or information to the user about how to reduce their fall risk in future walking exercises. In particular, the measurements can be analysed to provide feedback to the user about how long they should move before taking a rest, so as to avoid their fall risk reaching a level at which they are at a significant risk of falling. Thus, the measurements of the fall risk of the user obtained in step 101 can be analysed to determine a fall risk increase profile for the user. The fall risk increase profile indicates how and how quickly the fall risk of the user increases over time to the first threshold value while the user is moving. Where the fall risk measurements cover several time portions where the fall risk increases to the first threshold value while the user is moving, this step can comprise fitting a curve to the fall risk measurements for the various time portions to determine the profile, or modelling a typical fall risk increase profile using the measurements.

Once the fall risk increase profile has been determined, the profile is used to determine the maximum duration of a moving period for the user to reduce the likelihood of the fall risk exceeding the first threshold value while the user is moving. As an example, the maximum duration can be selected as the time taken for the fall risk to reach Y % of the first threshold value (e.g. 90%) according to the profile. The user interface 10 can be used to provide feedback to the user on the determined maximum duration. This feedback can be provided to the user at the start of a moving activity (e.g. walking, jogging, running, etc.), or whenever the maximum duration is determined.

In some cases, a user may be advised to exercise for a certain length of time each day. For example a user can be advised to walk for at least 30 minutes each day. Once the maximum duration is determined, the feedback can additionally indicate to the user that they should split their daily exercise requirement into multiple portions if the maximum duration is shorter than the length of time that they should exercise each day. For example, if a user is advised to exercise for 30 minutes per day but the maximum duration they can walk for before the fall risk exceeds the first threshold value (or otherwise becomes too high) is 12 minutes, then the feedback to the user can indicate that they should split the walk into three 10-minute segments.

Figure 5:
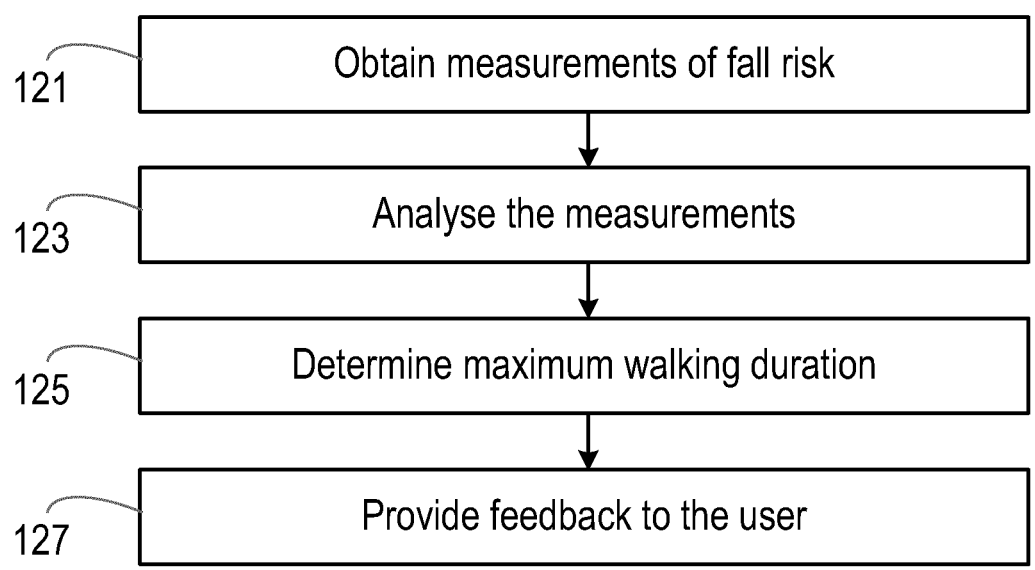
FIG. 5 is a flow chart illustrating a method of providing feedback to a user according to a second aspect.

It will be appreciated that an apparatus 2 can determine and provide feedback to the user about how to reduce their fall risk in future walking exercises independently from the feedback relating to the duration of a resting period described above. Therefore the flow chart in FIG. 5 illustrates a method of providing feedback to a user according to a second aspect. It will be appreciated that the method in FIG. 5 can be performed by apparatus 2, in particular by processing unit 4. The memory unit 4 or other data storage device can be used to store computer-readable code that, when executed by the processing unit 4 or other computing device, causes the processing unit 4 or other computing device to perform the method in FIG. 5.

In a first step, step 121, measurements of the fall risk of the user over a time period are obtained. The time period should comprise at least one time portion in which the fall risk of the user increases to a first threshold value while moving. Since these fall risk measurements are to be used to determine a fall risk increase profile for the user, ideally the time period covers several such time portions. It will be appreciated that the fall risk measurements do not have to cover a continuous time period, but could, for example, relate to measurements of the fall risk of the user when the user is moving over several different hours and/or days. The fall risk measurements may relate only to times when the user is performing a moving activity (e.g. walking, jogging or running), or they can relate to times when the user is not performing such an activity, for example including when the user is relaxing at home or sleeping.

Next, in step 123, the measurements of fall risk obtained in step 121 are analysed to determine a fall risk increase profile for the user. The fall risk increase profile indicates how and how quickly the fall risk of the user increases over time to the first threshold value while the user is moving. Where the fall risk measurements cover several time portions where the fall risk increases to the first threshold value while the user is moving, this step can comprise fitting a curve to the fall risk measurements for the various time portions to determine the profile, or modelling a typical fall risk increase profile using the measurements.

Once the fall risk increase profile has been determined in step 123, the profile is used in step 125 to determine the maximum duration of a moving period for the user to reduce the likelihood of the fall risk exceeding the first threshold value while the user is moving. As an example, the maximum duration can be selected as the time taken for the fall risk to reach Y % of the first threshold value (e.g. 90%) according to the profile.

Finally, in step 127, the user interface 10 can be used to provide feedback to the user on the determined maximum duration. This feedback can be provided to the user at the start of a moving activity (e.g. walking, jogging, running, etc.), or whenever the maximum duration is determined. The feedback provides the user with information about how long they should move before taking a rest, so as to avoid their fall risk reaching a level at which they are at a significant risk of falling. This feedback can therefore help the user to reduce their fall risk in future walking exercises by helping the user to schedule a regular rest during the activity.

In some embodiments the apparatus 2 described above can be configured such that the feedback provided to the user helps to educate the user or support the user in reducing their fall risk (or preventing the fall risk from increasing too much or at all) during future walks. This feedback can be based on fall risk measurements and optionally other information measured during previous walks, and potentially based on the responses to questions asked to the user (e.g. did you use a walking aid?). Based on the information the feedback provided to the user could advise the user to change the duration of the walk, change the speed of walking, change the number of breaks (e.g. rest breaks) during the walk, change the length of the breaks during the walk, avoid irregular or uneven surfaces during the walk, use a walking aid during the walk, wear a certain type of shoe during the walk, avoid walks when it is dark, avoid walks during bad weather conditions, etc.

Figure 6:
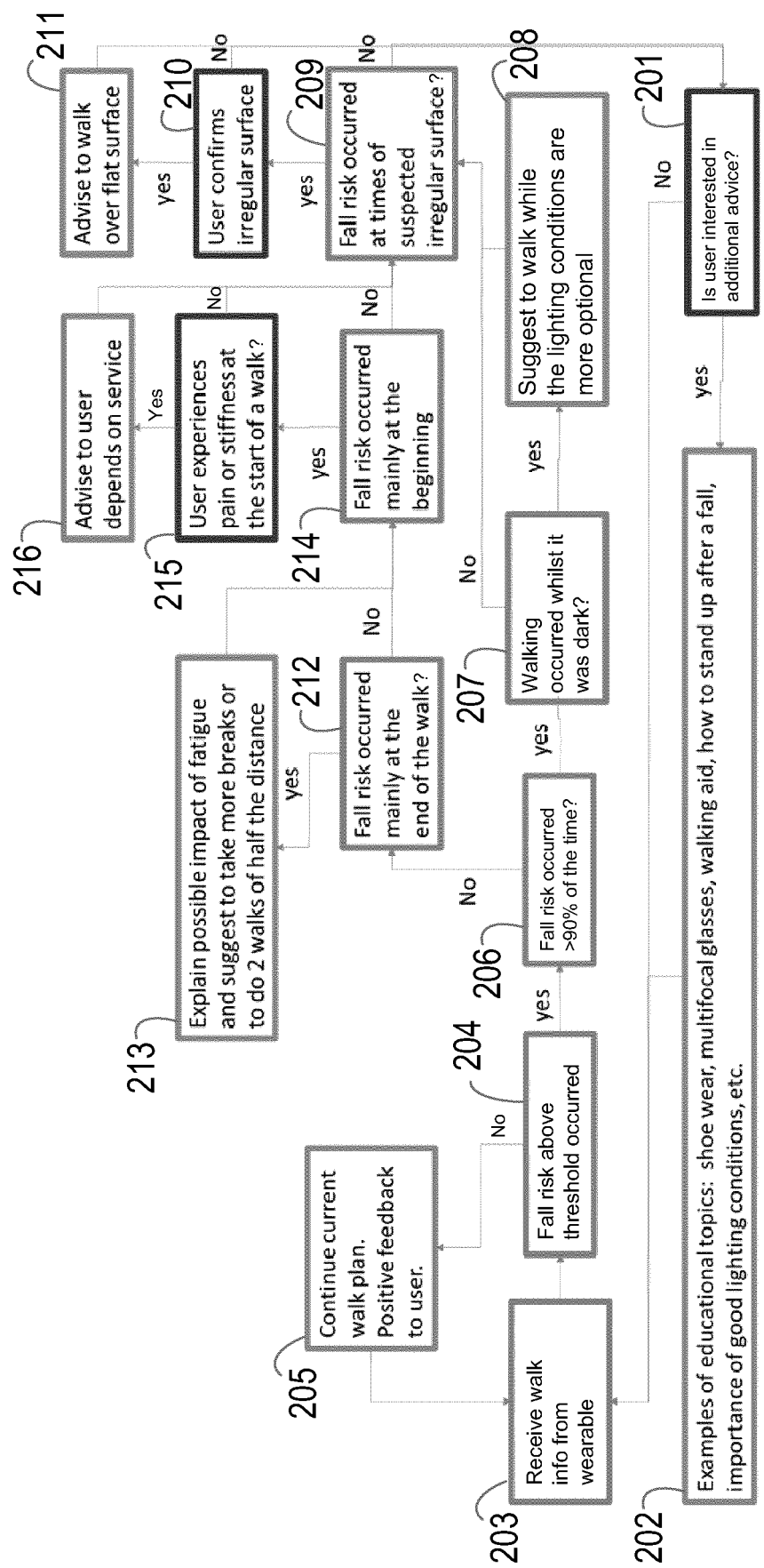
FIG. 6 is a flow chart illustrating a walking plan algorithm according to an embodiment.

The flow chart in FIG. 6 illustrates a specific embodiment of a walking planning algorithm. The algorithm shown in FIG. 6 is 'circular' in the sense that there is no clear defined start point, but instead the algorithm flows through the various steps over time to provide appropriate feedback to the user. The algorithm comprises various different types of steps or stages, including steps in which specific feedback is provided to the user, steps in which the algorithm obtains information from one or more sensors (e.g. sensor(s) 8 in the apparatus 2) and steps in which the algorithm requests information from the user (e.g. via a written or spoken question presented on the user interface 10).

Starting with step 201, the algorithm can ask the user whether they require additional advice relating to their fall risk or ways to reduce their fall risk. If the user responds positively, the algorithm can provide information to the user to educate them about things that increase their fall risk and/or things that the user can do to reduce their fall risk (step 202). For example, the information can include educational information on the type of shoes to wear, the wearing of multifocal glasses (or just glasses at all), the use of a walking aid, the best way to stand up after a fall, the importance of good lighting conditions, etc.

After step 202, or if the user responds negatively in step 201, the algorithm can receive information on the movements of the user (e.g. walking) from a wearable device or sensor (e.g. an accelerometer)—step 203. This information can be analysed to determine the fall risk and the fall risk can be compared to a threshold to determine if the fall risk has exceeded the threshold (step 204). If the fall risk has not exceeded the threshold, the algorithm can determine that the user should continue according to the current advice and walking plan, and the algorithm provides positive feedback to the user (step 205). The algorithm then returns to step 203. If it is determined that the fall risk has exceeded the threshold, the algorithm determines if the fall risk exceeded the threshold by more than a certain amount of the time (e.g. 90%)—step 206.

If not, then the algorithm can ask the user or otherwise determine if the walking activity occurred whilst it was dark (step 207). If yes, the algorithm can advise the user to walk when the lighting conditions are better/optimal (step 208). After step 208, or if the walking activity did not occur whilst it was dark, the algorithm can determine if the times of high fall risk (i.e. above the threshold) occurred at times where the user may have been walking on an irregular surface (step 209). If not, the algorithm can return to step 201 and ask the user if they require additional fall risk advice. If the algorithm determines that the high fall risk may have been caused by an irregular surface, the algorithm can ask the user to confirm whether or not this was the case (step 210). If the user confirms that the surface was irregular, the algorithm can advise the user to walk on a flat surface (step 211). The algorithm can then return to step 201. If the user confirms that the surface was not irregular, the algorithm can return to step 201.

If at step 206 it is determined that the fall risk did exceed the threshold for more than a certain amount of the time (e.g. 90%), the algorithm determines if the high fall risk mainly occurred at the end of the walking exercise/activity (step 212). If so, the algorithm can provide feedback to the user on the possible impact of fatigue and suggest to the user that they take more breaks or do two or more walks of a shorter distance (step 213). After step 213, or if the high fall risk did not occur mainly at the end of the walk, the algorithm determines if the high fall risk mainly occurred at the start of the walk (step 214). If not, the algorithm moves to step 209.

If the high fall risk mainly occurred at the start of the walk, the algorithm asks the user whether they experience pain or stiffness at the start of a walk (step 215). If so, the algorithm can provide advice to the user (step 216). The algorithm then moves to step 209. If the user does not experience pain or stiffness at the start of a walk, the algorithm moves to step 209.

It will be appreciated that the algorithm shown in FIG. 6 is merely exemplary, and the illustrated steps can occur in an alternative order, and/or the algorithm can include more or fewer steps than those shown.

There is therefore provided a method and apparatus for providing feedback to a user relating to the fall risk of the user and/or relating to advice to reduce the fall risk of the user.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for providing feedback to a user, the apparatus comprising:
a user interface for providing feedback to the user;
one or more sensors that measure movements of the user or one or more environmental parameters; and
a processing unit configured to:
obtain measurements of a fall risk of the user over a time period and information on a duration of resting periods occurring during the time period based on the movements of the user or the one or more environmental parameters measured by the one or more sensors, the time period comprising at least one time portion in which the fall risk of the user increases to a first threshold value while moving, the user rests for a resting period when the fall risk reaches the first threshold value, and the user subsequently resumes moving;
analyze the measurements of the fall risk of the user to determine the fall risk of the user at an end of each resting period when the user subsequently resumes moving and the duration of the resting period;
determine a fall risk recovery profile for the user from the duration of each resting period and the fall risk of the user at the end of each resting period;
determine the duration of a resting period required for the fall risk of the user to decrease to a second threshold value using the fall risk recovery profile; and
provide feedback to the user on the determined duration via the user interface.

2. An apparatus as claimed in claim 1, wherein the processing unit is configured to obtain the measurements and information by one of: retrieving the measurements of the fall risk and information from a memory unit in the apparatus, and receiving the measurements of the fall risk and information from another device or apparatus.

3. An apparatus as claimed in claim 1, wherein the processing unit is further configured to:
obtain further measurements of the fall risk of the user as the user is moving and compare the further measurements to the first threshold value; and
wherein the processing unit is configured to provide the feedback to the user on the determined duration if the further measurements exceed the first threshold value.

4. An apparatus as claimed in claim 3, wherein the processing unit is further configured to:
determine an updated fall risk recovery profile from the measurements of the fall risk of the user, information on the duration of the resting period and the further measurements of the fall risk of the user; and
determine an updated resting period duration required for the fall risk of the user to decrease from the first threshold value to a second threshold value using the updated fall risk recovery profile.

5. An apparatus as claimed in claim 3, wherein the further measurements of the fall risk are obtained in real time or near real time.

6. An apparatus as claimed in claim 1, wherein the processing unit is further configured to:
analyze the measurements of the fall risk of the user to determine a fall risk increase profile for the user, the fall risk increase profile indicating how the fall risk of the user increases over time to the first threshold value while the user is moving;
determine the maximum duration of a moving period for the user to reduce the likelihood of the fall risk exceeding the first threshold value while the user is moving; and
provide feedback to the user on the determined maximum duration of the moving period via the user interface.

7. An apparatus as claimed in claim 1, wherein the movements of the user comprise walking, jogging or running.

8. A method of providing feedback to a user, the method in an apparatus comprising:
measuring movements of the user or an environmental parameter;
obtaining measurements of a fall risk of the user over a time period and information on a duration of resting periods occurring during the time period based on the measured movements of the user or an environmental parameter, the time period comprising at least one time portion in which the fall risk of the user increases to a first threshold value while moving, the user rests for a resting period when the fall risk reaches the first threshold value, and the user subsequently resumes moving;
analyzing the measurements of the fall risk of the user to determine the fall risk of the user at an end of each resting period when the user subsequently resumes moving and the duration of the resting period;
determining a fall risk recovery profile for the user from the duration of each resting period and the fall risk of the user at the end of each resting period;
determining the duration of a resting period required for the fall risk of the user to decrease to a second threshold value using the fall risk recovery profile; and
providing feedback to the user on the determined duration via a user interface in the apparatus.

9. A method as claimed in claim 8, wherein the step of obtaining comprises obtaining the measurements and information by one of: retrieving the measurements of the fall risk and information from a memory unit in the apparatus.

10. A method as claimed in claim 8, wherein the method further comprises:
obtaining further measurements of the fall risk of the user as the user is moving and comparing the further measurements to the first threshold value; and
wherein the step of providing feedback comprises providing the feedback to the user on the determined duration if the further measurements exceed the first threshold value.

11. A method as claimed in claim 10, wherein the method further comprises:
determining an updated fall risk recovery profile from the measurements of the fall risk of the user, information on the duration of the resting period and the further measurements of the fall risk of the user; and
determining an updated resting period duration required for the fall risk of the user to decrease from the first threshold value to a second threshold value using the updated fall risk recovery profile.

12. A method as claimed in claim 10, wherein the further measurements of the fall risk are obtained in real time or near real time.

13. A method as claimed in claim 8, wherein the method further comprises:
analyzing the measurements of the fall risk of the user to determine a fall risk increase profile for the user, the fall risk increase profile indicating how the fall risk of the user increases over time to the first threshold value while the user is moving;

determining the maximum duration of a moving period for the user to reduce the likelihood of the fall risk exceeding the first threshold value while the user is moving; and providing feedback to the user on the determined maximum duration of the moving period via the user interface.

14. A method as claimed in claim 8, wherein the movements of the user comprise walking, jogging or running.

15. A computer program product comprising a computer readable medium having computer readable code embodied therein, the computer readable code being configured such that, on execution by a suitable computer or processing unit, the computer or processing unit is caused to perform the method of claim 8.

* * * * *